United States Patent [19]
Roth et al.

[11] Patent Number: 5,856,497
[45] Date of Patent: Jan. 5, 1999

[54] ASYMMETRIC SYNTHESIS OF α-CYCLOALKYLALKYL SUBSTITUTED METHANAMINES

[75] Inventors: Gregory Roth, New Milford, Conn.; John Landi, Gardner, Mass.

[73] Assignee: Boehringer Ingelheim Pharmaceuticals, Inc., Ridgefield, Conn.

[21] Appl. No.: 755,748

[22] Filed: Nov. 22, 1996

Related U.S. Application Data

[60] Provisional application No. 60/008,468, Dec. 11, 1995.
[51] Int. Cl.$^6$ .................. C07D 213/02; C07C 211/01
[52] U.S. Cl. ............................. 546/285; 564/336
[58] Field of Search .............. 546/285; 564/336

[56] References Cited

U.S. PATENT DOCUMENTS

| | | | |
|---|---|---|---|
| 4,595,531 | 6/1986 | Milkowski et al. | 540/573 |
| 4,598,093 | 7/1986 | Tahara et al. | 514/538 |
| 5,169,971 | 12/1992 | Inomata et al. | 558/338 |
| 5,296,486 | 3/1994 | Lazer et al. | 514/333 |

OTHER PUBLICATIONS

March, J. Advanced Organic Chemistry: Reactions, Mechanisms, and Structure, 1992, 4th edition, Wiley & Sons, Inc., pp. 822–825 and 1168.
Mancuso, A.J. et al, Synthesis, 1981, pp. 165–185.
Morrison, R.T. et al, Organic Chemistry, 4th edition, 1983, Allyn & Bacon, Inc., p. 250.
Chen, Y. et al, Synth. Comm. 1989, 19(7–8), pp. 1423–1430, online results only.
Chen, Y. et al, Huaxue Xuebao, 1990, 48(11), pp. 1131–1135, online results only.
Lazer, E.S. et al, J. Med. Chem. 1994, 37, pp. 913–923.
Aiqiao, M. et al, Synth. Comm. 1991, 21(22), pp. 2207–2212.
Carlson, R.G. et al, J. Org. Chem. 1971, 36(16), pp. 2319–2324.
Jefford, C.S. et al, Tetrahedron Lett. 1994, 35(34), pp. 6275–6278.
Chen, Y. et al, Synth. Commun. 1989, 19(7–8), pp. 1423–1430.
European Search Report for Appl. No. EP 96 11 9658, (May 2, 1997).

Erdik, E. and Matteson, D.S., "Kinetics of Osmium Tetraoxide Catalyzed Trimethylamine N–Oxide Oxidations of Cyclohexene and α–Pinene to Diols," *J. Org. Chem.*, 54:2742–2748 (1989).
Ray, R. and Matteson, D.S., "Osmium Tetroxide Catalyzed Hydroxylation of Hindered Olefins," *Tetrahedron Letters* 21:449–450 (1980).
Aiqiao, M. et al., "Asymmetric Synthesis XV: Enantioselective Syntheses of (R) or (S)–α–substituted–(2–Pyridyl) Methylamines Via Chiral Pinanone Ketimine Template," *Synthetic Communications 21(21)*:2207–2212 (1991).
Dondoni, A. et al., "Alkylation of Camphor and Pinanone Imines of 2–(Aminomethyl)thiazole. Enantioselective Synthesis of 2–(1–Aminoalkyl)thiazoles," *Synthesis* 5:641–646 (May 1996).
Miao, C. et al., "A Simple and Effective Enantiomeric Synthesis Of A Chiral Primary Amine," *Tetrahedron Letters 34(14)*:2259–2262 (1993).
Yuanwei, C. et al., "Asymmetric Synthesis VIII: Enantioselective Synthesis of (R) or (S)–α–Subsituted Benzylamines Via Chiral Pinanone Ketimine Template," *Synthetic Communications 19(7/8)*:1423–1430 (1989).
Yuanwei, C. et al., "Asymmetric synthesis of optically active–α–substituted benzylamines," *Chem. Abstracts 114(1)*: 592, Abstract No. 6009d (1991).
Ray, R. and Matteson, D.S., "A Highly Efficient Osmium Tetroxide Catalyzed Oxidation of Sterically hindered Olefins to Diols," *J. Indian Chem. Soc.* 59(2):119–23 (Feb. 1982).
VanRheenen, V. et al., "An Improved Catalytic OsO4 Oxidation of Olefins to Cis–1,2–glycols Using Tertiary Amine Oxides as the Oxidant," *Tetrahedron Letters*, 23:1973–1976 (1976).

*Primary Examiner*—Alan L. Rotman
*Assistant Examiner*—Charanjits S. Aulakh
*Attorney, Agent, or Firm*—Robert P. Raymond; Alan R. Stempel; Mary-Ellen Devlin

[57] ABSTRACT

This invention relates to process for asymmetrically producing enantiomerically pure α-cycloalkylalkyl substitututed methanamines from α-pinene. One key step of the process of this invention utilizes the oxidation product of α-pinene, hydroxy pinanone, as a chiral auxiliary to direct the stereoselective alkylation of the corresponding ketimine. This invention also relates to key intermediates useful in the processes referred to herein.

21 Claims, No Drawings

ASYMMETRIC SYNTHESIS OF α-CYCLOALKYLALKYL SUBSTITUTED METHANAMINES

This application claims benefit of USC Provisional Appl. No. 60/008,468, filed Dec. 11, 1995.

TECHNICAL FIELD OF INVENTION

This invention relates to processes for asymmetrically producing enantiomerically pure α-cycloalkylalkyl substituted methanamines from α-pinene. One key step of the process of this invention utilizes the oxidation product of α-pinene, hydroxy pinanone, as a chiral auxiliary to direct the stereoselective alkylation of the corresponding ketimine. This invention also relates to key intermediates useful in the processes referred to herein. The processes and intermediates of this invention are useful in the preparation of enantiomerically pure, pharmaceutically active compounds, such as (S)-N-[2-cyclohexyl-1-(2-pyridinyl)ethyl]-5-methyl-2-benzoxazolamine (ontazolast).

BACKGROUND OF THE INVENTION

α-Cycloalkylalkyl substituted methanamines constitute an important class of intermediates used in the production of various substituted 2-benzoxazoles, 2-benzothiazoles, 2-oxazolpyridines and 2-thiazolopyridines, which compounds are potent leukotriene biosynthesis inhibitors. Examples of such compounds are described in commonly-owned U.S. Pat. No. 5,296,486, issued Mar. 22, 1994 and in Lazer et al, *J. Med. Chem*, 37, pp. 913–23 (1994). Such inhibitors are effective drugs in the treatment of particular disease states involving leukotriene biosynthesis, such as asthma.

Others have reported various synthetic schemes for the production of certain α-cycloalkylalkyl substituted methanamines and structurally similar compounds. For example, production of a racemic mixture of α-cyclohexylmethyl-2-pyridimenethanamine described in P. L. Pickard and T. L. Tolbert, *J. Org. Chem.*, 26, pp. 4886–88 (1961). That method reacts 2-cyanopyridine with an organometallic reagent such as cyclohexylmethylmagnesium bromide to form a ketimine intermediate, which is then reduced in situ. An asymmetric synthesis of (S)-α-substituted benzylamines and pyridylamines is reported in M. Aiqiao et al., *Synthetic Communications*, 21, pp. 2207–12 (1991). In addition, an asymmetric synthesis of (S)-α-substituted benzylamines using ketimines derived from 2-hydroxy-3-pinanone is described in C. Yuanwei et al., *Synthetic Communications*, 19, pp. 1423–30 (1989). Furthermore, ketimines of 2-hydroxy-3-pinanone have been used for the synthesis of various α-amino acids and α-alkyl benzylamines (see, for example, S. I. Yamada et al., *J. Chem. Soc. Chem. Comun.*, pp. 136–37 (1976); T. Oguri et al., *Chem. Pharm. Bull.*, 26, pp. 803–808 (1978); A. Solladie-Cavallo and M. C. Simon, *Tetrahedron Lett.*, 30, pp. 6011–14 (1989)).

All of these conventional methods for producing α-cycloalkylalkyl substituted methanamines and structurally related compounds suffer from one or more disadvantages, including numerous and cumbersome process steps, use of expensive or commonly unavailable reagents, low overall yields and low to moderate stereoselectivity. In addition, those conventional methods are generally not suitable for use on an industrial scale.

BRIEF DESCRIPTION OF THE INVENTION

This invention solves the above mentioned problems by providing convenient processes for asymmetrically producing of α-cycloalkylalkyl substituted methanamines from α-pinene. The processes of this invention use inexpensive and commercially available reagents and result in high overall yields and retained enantiopurity. These processes are especially well suited for the production of α-cycloalkylalkyl-2-pyridinemethanamines on an industrial scale.

According to a preferred embodiment, this invention relates to a process for producing an α-cycloalkylalkyl-2-pyridinemethanamine comprising the steps of:

(a) oxidizing α-pinene with potassium permanganate using a phase transfer catalyst in an appropriate solvent to form 2-hydroxy-3-pinanone;

(b) reacting the 2-hydroxy-3-pinanone with 2-(aminomethyl)pyridine and a Lewis acid catalyst in toluene or methyl t-butyl ether to form 2-hydroxy-3-(pyridinemethyl) ketimine;

(c) deprotonating the 2-hydroxy-3-(pyridinemethyl) ketimine using a strong base;

(d) reacting about 1 equivalent of the deprotonated ketimine with about 1–2 equivalents of a cycloalkylalkyl halide at a temperature of between about −20° C. and about 50° C. to form α-cycloalkylalkyl-2-hydroxy-3-(pyridinemethyl) ketimine; and (e) hydrolyzing the (S)-α-cycloalkylalkyl-2-hydroxy-3-(pyridinemethyl) ketimine.

In another preferred embodiment, this invention relates to a process for producing an α-cycloalkylalkyl-2-pyridinemethanamine comprising the steps of:

(a) reacting α-pinene with catalytic potassium osmate in a solution of pyridine, N-methylmorpholine-N-oxide and aqueous acetone to form cis-pinanediol;

(b) oxidizing cis-pinanediol with DMSO activated by pyridine.$SO_3$ and triethylamine in an appropriate solvent to form 2-hydroxy-3-pinanone;

(c) reacting the 2-hydroxy-3-pinanone with 2-(aminomethyl)pyridine and a Lewis acid catalyst in toluene or methyl t-butyl ether to form 2-hydroxy-3-(pyridinemethyl) ketimine;

(d) deprotonating the 2-hydroxy-3-(pyridinemethyl) ketimine using a strong base;

(e) reacting about 1 equivalent of the deprotonated ketimine with about 1–2 equivalents of a cycloalkylalkyl halide at a temperature of between about −20° C. and about 5° C. to form α-cycloalkylalkyl-2-hydroxy-3-(pyridinemethyl) ketimine; and (f) hydrolyzing the (S)-α-cycloalkylalkyl-2-hydroxy-3-(pyridinemethyl) ketimine.

In a further embodiment, this invention relates to intermediates useful in the above described processes having the structural formula (I):

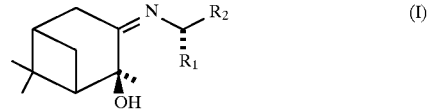

wherein:

$R_1$ is —$(CH_2)_n$-cycloalkyl, said cycloalkyl being unsubstituted or substituted with $C_1$–$C_4$ alkyl, $C_1$–$C_4$ alkoxy, hydroxy, amino or halo;

$R_2$ is selected from the group consisting of an unsubstituted or substituted phenyl or naphthyl ring wherein the ring substituents are selected from the group consisting of halo, hydroxy, amino, $C_1$–$C_4$ alkyl and $C_1$–$C_4$ alkoxy; 3-methyl-1,2,4-oxadiazol-5-yl; 2- or 3-thienyl; 2-, 3-, or 4-pyridyl, unsubstituted or substituted with halo, hydroxy, amino, $C_1$–$C_4$ alkyl and $C_1$–$C_4$ alkoxy; 2-imidazole, unsubstituted or substituted on the nitrogen with methyl; 2-thiazole, unsubstituted or substituted at the 4-position with methyl; —C(O)$R_3$; —CH$_2$O ($C_1$–$C_4$ alkyl); CH$_2$S($C_1$–$C_3$ alkyl); —CH$_2$SO$_2$($C_1$–$C_3$ alkyl); —CH$_2$NH$_2$; —CH$_2$NHSO$_2$ ($C_1$–$C_3$ alkyl)$_2$; and —CH$_2$OC(O)NH($C_1$–$C_3$ alkyl);

$R_3$ is selected from the group consisting of $C_1$–$C_3$ alkyl, phenyl and 1-methylimidazol-2-yl; and n is an integer from 0–4.

DETAILED DESCRIPTION OF THE INVENTION

Unless otherwise noted, the following definitions apply:

The term "alkyl", as used herein alone or in combination with other terms, refers to a $C_1$–$C_4$ branched or unbranched alkyl radical. Examples of such alkyl radicals include, but are not limited to, methyl, ethyl, propyl, butyl, isopropyl and isobutyl. Preferably, the alkyl radicals are selected from the group consisting of methyl, ethyl and propyl. More preferably, the alkyl radicals are selected from the group consisting of methyl and ethyl. Most preferably, the alkyl radical is methyl.

The term "cycloalkyl", as used herein alone or in combination with other terms, refers to an unsubstituted three to eight membered carbocyclic radical or a three to eight membered carbocyclic radical substituted with $C_1$–$C_4$ alkyl, $C_1$–$C_4$ alkoxy, hydroxy, amino or halo. Preferably, the cycloalkyl radical is a cyclopentyl, cyclohexyl or cyclooctyl radical, said radical being unsubstituted or substituted with hydroxy or halo. More preferably, the cycloalkyl radical is a cyclohexyl unsubstituted or substituted with hydroxy or halo. Most preferably, the cycloalkyl radical is unsubstituted cyclohexyl.

The term "enantiomerically pure" refers to a compound or compounds that have are present in enantiomeric excess of greater than about 90%. Preferably, the enantiomeric excess is greater than about 93% and more preferably, the enantiomeric excess is greater than about 97%. Most preferably, the enantiomeric excess is greater than about 98%.

The term "halo", as used herein alone or in combination with other terms, refers to a chloro, bromo, fluoro or iodo radical. Preferably, the halo radical is a fluoro radical.

The terms "hydroxy pinanone"or "2-hydroxy-3-pinanone" are used interchangeably and unless otherwise specified, refer to either the (R) or (S) isomer, or a racemic mixture of both isomers.

The term "pyridyl" or "pyridine" as used herein alone or in combination with other terms, refers to a pyridyl radical attached to a specified chemical group at the 2-, 3- or 4- position, wherein said pyridyl radical is unsubstituted or substituted with halo, hydroxy, amino, $C_1$–$C_4$ alkyl and $C_1$–$C_4$ alkoxy. Preferably, the pyridyl radical is unsubstituted 2- or 3-pyridyl. More preferably, the pyridyl radical is unsubstituted 2-pyridyl.

The generic chemical formulas referred to herein expressly include only those combinations of substituents that give rise to stable chemical structures. A stable chemical structure is one that retains its structural integrity when used under the reaction conditions recited herein. In general, such a structure will be stable at a temperature of about 0° C. for a period of at least one day. Such stable chemical structures will be easily identified by those of ordinary skill in the art of organic chemical synthesis.

As the person of ordinary skill in the art will also appreciate, there are several acceptable ways to name the chemical compounds referred to herein. Although we believe that the nomenclature we have used is clear and unambiguous, there may be places where the chemical drawings and the chemical names may be subject to different interpretations. In those cases, it is expressly provided that the structures as shown in the drawings will control.

The processes of this invention, taken together as a synthetic scheme, provide efficient synthetic routes to enantiomerically pure α-cycloalkylalkyl substituted methanamines. These processes can be advantageously run on an industrial scale. The starting material used in the processes of this invention is α-pinene. Although the preferred processes of this invention use (S)-(–)- α-pinene, it should be understood that either enantiomer may be used to obtain a final cycloalkylalkyl-pyridinemethanamine product having the corresponding stereochemistry. Both stereoisomers of α-pinene (i.e., (R)-(+)-α-pinene and , (S)-(–)-α-pinene) are relatively inexpensive and commercially available in bulk lots of different enantiomeric purities (for example, from Aldrich Chemical Company, Milwaukee, Wis.). Typically, commercially available α-pinene may be obtained in enantiomeric excess of at least approximately 70–95%. The preferred commercial α-pinene for use in the processes described herein is about 93% e.e. (S)-(–)-α-pinene.

Advantageously, the enantiomeric purity of the starting material is retained and, in some cases, enhanced, during the processes of this invention. Therefore, the greater the enantiomeric excess of α-pinene used initially, the greater the enantiomeric excess of the resultant α-cycloalkylalkyl substituted methanamine. The enantiomeric excess of commercially available α-pinene may optionally be further enriched using known methods, such as the method described in Brown et al., *J. Org. Chem.,* 47, pp. 4583–84 (1982). Prior to oxidation in the processes of this invention, we prefer that the α-pinene starting material contains an enantiomeric excess greater than about 90%. Preferably, the enantiomeric excess is greater than about 93% and more preferably, the enatiomeric excess is greater that about 97%. Most preferably, the enantiomeric excess of the α-pinene starting material is greater than about 98%.

In the processes of this invention, α-pinene is converted to the corresponding (R)- or (S)-2-hydroxy-3-pinanone. In this process, production of the (R) isomer of 2-hydroxy-3-pinanone is preferred (derived from (S)-(–)- α-pinene as shown below in Scheme 1). 2-hydroxy-3-pinanone is a known chiral auxiliary for the enantioselective synthesis of α-amino acids, but its utility in asymmetric syntheses has been limited, due in part to its limited availability in high enantiomeric excess and its prohibitively high catalog cost. Previously, there was no efficient, scalable and cost-effective way to produce 2-hydroxy-2-pinanone from α-pinene. In fact, the only reported route to 2-hydroxy-3-pinanone from α-pinene is the potassium permanganate oxidation of α-pinene in aqueous acetone solution (R. G. Carlson and J. K. Pierce, *J. Org. Chem.,* 36, pp. 2319–24 (1971)). This method has not been utilized commercially because it is not amenable to scale-up and the reported yield is variable and modest (32–48%). In addition, the published reaction sequence is potentially explosive and therefore, too hazardous to consider for large scale processing (L. Bretherick, *Handbook of Reactive Chemical Hazards,* 4th ed., p. 1295 (Butterworth & Co.,1990)).

The processes of this invention provide two new synthetic routes to produce 2-hydroxy-3-pinanone from α-pinene. These two reaction sequences are summarized in Scheme 1:

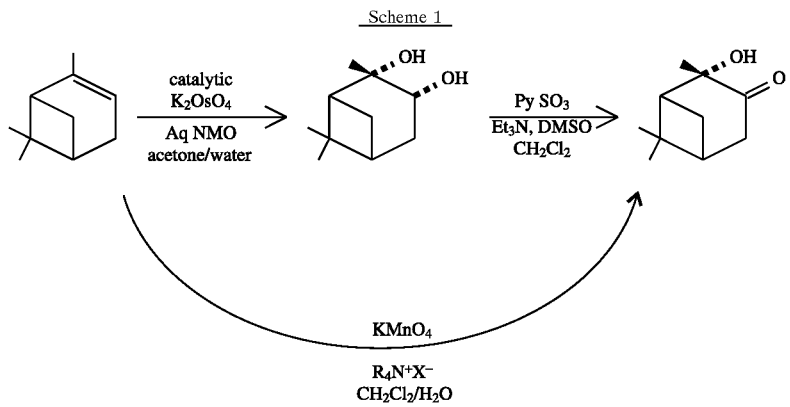

One route provides a two step oxidation sequence, involving cis-dihydroxylation of α-pinene using catalytic amounts of potassium osmate, followed by subsequent oxidation of the diol to the hydroxyketone. Specifically, the first step of this process uses a mixture of α-pinene, pyridine, 4-methylmorpholine oxide and potassium osmate dihydrate in aqueous acetone, which is reacted at a temperature between about 0° C. and about 60° C. (reflux temperature) for a period of about 10 hours to several days, but preferably, the reaction mixture is refluxed for about 10 to about 48 hours. Preferably, the reaction mixture is refluxed for about 10 to about 40 hours and, most preferably, for about 20 to about 35 hours.

It was discovered that as little as about 0.002 equivalents of osmium can be used in the dihydroxylation reaction without loss of efficiency. Inexpensive aqueous NMO was found to be as effective as anhydrous solid NMO in this reaction. The dihydroxylation can be run at high concentrations (up to about 1.5M) without any adverse effect, advantageously making this a volume-efficient reaction. Preferably the following reagents are used in this process step: $K_2OsO_4 \cdot 2H_2O$ (about 0.002 equivalents), aqueous NMO (about 1.2 equivalents), pyridine (about 1.2 equivalents), and acetone/water (in a ratio of about 5:1). At reflux temperature, 98% conversion is seen at about 29 hours. This reaction step typically results in approximately 85–95% yield of cis-dihydroxylated α-pinene. The only identified by-product was 2-hydroxy-3-pinanone (about 5%–10% under standard conditions), the desired end-product of the two-step oxidation sequence.

Following dihydroxylation, the cis-diol is further oxidized to 2-hydroxy-3-pinanone using DMSO activated by pyridine.$SO_3$ complex in an appropriate solvent. Preferably, an excess of triethylamine is used also present and the preferred solvent is methylene chloride. It was discovered that these oxidation reagents resulted in an economical process that could be easily worked-up and produced the desired product in high yield. The reaction temperature should preferably be between about 0° C. and about 25° C., but more preferably between about 10+ C. and about 25° C. Preferably, the reactants are present in the following approximate amounts: pyridine.$SO_3$ (3 equivalents), DMSO (7–8 equivalents) and triethylamine (4 equivalents). Although all conventional means for isolating 2-hydroxy-3-pinanone are envisioned by this invention, it was found that the product can be most easily isolated in high purity by distillation (in yields ranging from about 70% to about 85%). On a 500 g scale, this reaction sequence resulted in an overall yield of about 76%. The two-step reaction sequence from α-pinene to 2-hydroxy-3-pinanone described above results in a product having the same optical purity as the starting material, indicating that the optical purity is maintained during these transformations.

As an alternative to the two-step oxidation reaction, this invention also provides a one-step route which also yields enantiomerically pure 2-hydroxy-3-pinanone from α-pinene. As an initial matter, we followed a conventional protocol using potassium permanganate in acetone/water (see R. G. Carlson and J. K. Pierce, cited above). The reaction proceeded to the expected product, but resulted in a moderate 42% yield of 2-hydroxy-3-pinanone (approximately half the overall yield obtained using the above described two-step oxidation sequence). In addition, this reaction sequence is potentially explosive and therefore, too hazardous for large scale use (as detailed above).

It was discovered that the yield of 2-hydroxy-3-pinanone could be equalled or improved while entirely avoiding the safety hazard by performing the one-step potassium permanganate oxidation reaction with a phase transfer catalyst in an appropriate solvent. It is well known that phase-transfer catalyzed oxidations tend to be unworkable on a commercial scale because manganese dioxide precipitates as a finely divided solid which is difficult to filter away from the reaction mixture. Although in principle, it would be possible to stabilize the intermediate manganese species to prevent their disproportionation to manganese dioxide (e.g., by complexation with polyphosphoric acid) and to electrochemically regenerate permanganate, in practice this stabilization is very difficult to accomplish. We have found, surprisingly, that the phase transfer reaction of α-pinene runs smoothly under the conditions described herein.

Appropriate solvents for the phase transfer oxidation step are organic solvent/water solvents where the ratio of organic solvent to water is between about 1:5 to about 5:1. Suitable organic solvents include, but are not limited to, chloronated hydrocarbons (such as methylene chloride and dichloroethane), xylene and toluene. The preferred solvent for use in this process step is methylene chloride/water in a ratio of about 1:1. Phase transfer catalysts useful in the processes of this invention are those that have large extraction constants and include, but are not limited to, quaternary ammonium, phosphonium and arsonium salts, crown ethers and linear polyethers (such as dialkyl ethers of polythylene glycol). The preferred phase transfer catalysts for this reaction step are quaternary ammonium salts, and more preferably, the phase transfer catalyst is methyl tributyl ammonium chloride.

In a further process of this invention, chiral 2-hydroxy-3-pinanone is condensed with a primary amine using a Lewis acid catalyst in toluene or methyl t-butyl ether to produce the corresponding ketimine, as shown in Scheme 2:

Scheme 2

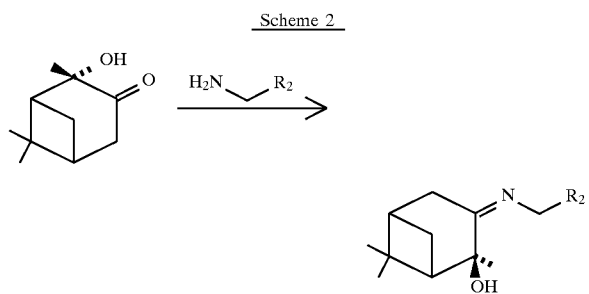

wherein:
$R_2$ is selected from the group consisting of an unsubstituted or substituted phenyl or naphthyl ring wherein the ring substituents are selected from the group consisting of halo, hydroxy, amino, $C_1$–$C_4$ alkyl and $C_1$–$C_4$ alkoxy; 3-methyl-1,2,4-oxadiazol-5-yl; 2- or 3-thienyl; 2-, 3-, or 4-pyridyl, unsubstituted or substituted with halo, hydroxy, amino, $C_1$–$C_4$ alkyl and $C_1$–$C_4$ alkoxy; 2-imidazole, unsubstituted or substituted on the nitrogen with methyl; 2-thiazole, unsubstituted or substituted at the 4-position with methyl; —C(O)$R_3$; —CH$_2$O(C$_1$–C$_4$ alkyl); CH$_2$S(C$_1$–C$_3$ alkyl); —CH$_2$SO$_2$(C$_1$–C$_3$ alkyl); —CH$_2$NH$_2$; —CH$_2$NHSO$_2$(C$_1$–C$_3$ alkyl)$_2$; and —CH$_2$OC(O)NH(C$_1$–C$_3$ alkyl); and $R_3$ is selected from the group consisting of $C_1$–$C_3$ alkyl, phenyl and 1-methylimidazol-2-yl.

Preferably, $R_2$ is selected from 2-, 3-, or 4-pyridyl, wherein said pyridyl is unsubstituted or substituted with halo, hydroxy, amino, $C_1$–$C_4$ alkyl and $C_1$–$C_4$ alkoxy. Preferably, $R_2$ is an unsubstituted 2- or 3-pyridyl. More preferably, $R_2$ is unsubstituted 2-pyridyl. The preferred primary amine for use in the reaction shown in Scheme 2 is pyridyl methylamine and more preferably, 2-(aminomethyl) pyridine.

The stereochemistry shown above in Scheme 2 illustrates the condensation reaction of (R)-hydroxypinanone with a primary amine. It will be appreciated by those of ordinary skill in the art that the condensation reaction works equally well using the (S) isomer of hydroxypinanone.

Condensation reactions similar to those shown in Scheme 2 have been previously reported using benzene as the solvent and BF$_3$.Et$_2$O as the catalyst. However, benzene is not favored in the manufacturing process because of its toxicity and boron trifluoride etherate is not compatible with common laboratory equipment because of its inherently corrosive properties. Advantageously, we have found that use of toluene or methyl t-butyl ether results in an efficient and economic reaction for use on an industrial scale. Preferably, the condensation reaction in toluene or methyl t-butyl ether is carried out at reflux temperature for about 1 to about 4 hours, with azeotropic removal of water.

Although the condensation reaction may proceed without a catalyst, yields are typically low (i.e., below about 50%).

Therefore, we prefer use of a Lewis acid catalyst. The preferred Lewis acid catalysts are titanium isopropoxide, thionyl chloride and acetic acid. Thionyl chloride is most preferred. When titanium isopropoxide is the Lewis acid catalyst, the reaction proceeds best when at least about 10 mole % of titanium isopropoxide is used. It was discovered that use of lesser amounts of titanium isopropoxide (e.g., 1–5%) increases the reaction time and tends to decrease the quality of the ketimine product. The most preferred amound of thionyl chloride is from about 1% to about 5%. Once the solvent is removed from the reaction mixture, the crude ketimine can be used directly in the next step.

The ketimine produced in Scheme 2 may be stereoselectively alkylated using the method shown in Scheme 3:

Scheme 3

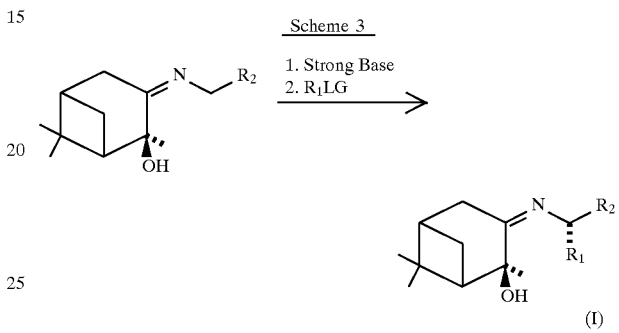

(I)

wherein:
$R_1$ is —(CH$_2$)$_n$-cycloalkyl, said cycloalkyl being unsubstituted or substituted with $C_1$–$C_4$ alkyl, $C_1$–$C_4$ alkoxy, hydroxy, amino or halo;

$R_2$ is selected from the group consisting of an unsubstituted or substituted phenyl or naphthyl ring wherein the ring substituents are selected from the group consisting of halo, hydroxy, amino, $C_1$–$C_4$ alkyl and $C_1$–$C_4$ alkoxy; 3-methyl-1,2,4-oxadiazol-5-yl; 2- or 3-thienyl; 2-, 3-, or 4-pyridyl, unsubstituted or substituted with halo, hydroxy, amino, $C_1$–$C_4$ alkyl and $C_1$–$C_4$ alkoxy; 2-imidazole, unsubstituted or substituted on the nitrogen with methyl; 2-thiazole, unsubstituted or substituted at the 4-position with methyl; —C(O)$R_3$; —CH$_2$O(C$_1$–C$_4$ alkyl); CH$_2$S(C$_1$–C$_3$ alkyl); —CH$_2$SO$_2$(C$_1$–C$_3$ alkyl); —CH$_2$NH$_2$;—CH$_2$NHSO$_2$(C$_1$–C$_3$ alkyl)$_2$; and —CH$_2$OC(O)NH(C$_1$–C$_3$ alkyl);

$R_3$ is selected from the group consisting of $C_1$–$C_3$ alkyl, phenyl and 1-methylimidazol-2-yl;

n is an integer from 0–4; and

LG is a leaving group.

Examples of suitable leaving groups (LG) for the process shown in Scheme 3 include conventional leaving groups, which will be readily identified by those of ordinary skill in the art. For example, common leaving groups for nucleophilic substitution reactions such as that described in Scheme 3 are described in organic chemistry textbooks, such as J. March, *Advanced Organic Chemistry: Reactions, Mechanisms and Structure*, 3rd ed., John Wiley & Sons (1985). Preferred leaving groups include halides and sulfonyl leaving groups (such as tosylates, brosylates, nosylates, mesylates, triflates, nonaflates and treslates). The most preferred leaving groups are iodide and bromide.

Preferably, $R_1$ is cyclohexylmethyl, wherein the cyclohexyl is unsubstituted or substituted with $C_1$–$C_4$ alkyl, $C_1$–$C_4$ alkoxy, hydroxy or halo (and more preferably, $R_1$ is cyclohexylmethyl, unsubstituted or substituted with hydroxy or halo; and most preferably, $R_1$ is unsubstituted cyclohexylmethyl).

Preferably, $R_2$ is selected from 2-, 3-, or 4-pyridyl, wherein said pyridyl is unsubstituted or substituted with halo, hydroxy, amino, $C_1$–$C_4$ alkyl and $C_1$–$C_4$ alkoxy. Preferably, $R_2$ is an unsubstituted 2- or 3-pyridyl. More preferably, $R_2$ is unsubstituted 2-pyridyl.

The preferred ketimines of formula (I) are those having the structure of formulas (II), (III) and (IV):

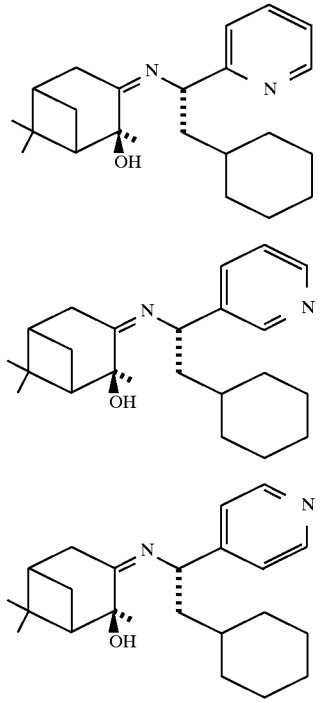

Although limited examples of alkylation of ketimines using alkyl halides are known (see, for example, Aiqiao et al., cited above), significantly more than 2 equivalents of alkyl halide are typically used and the reaction is carried out at a extremely low temperature (typically around −78° C.). These features make the conventional alkylation reaction of ketamines expensive and unworkable on a commercial scale. Surprisingly, we have discovered that the reaction shown in Scheme 3 is an excellent stereoselective process that can be run with less alkyl halide and at a higher temperature than previously known. The reaction of Scheme 3 comprises two steps: (a) deprotonating the ketimine with a strong base, then (b) reacting about 1 equivalent of the deprotonated ketimine with about 1–2 equivalents of an alkyl halide at a temperature of between about −200° C. and about 0° C. The preferred strong bases for this reaction are lithium diisopropylamide and n-butyllithium (and more preferably, the strong base is n-butyllithium). We prefer using about 1 equivalent of a cycloalkyl alkyl iodide or about 2 equivalents of cycloalkylalkyl bromide in this reaction step. The preferred cycloalkylalkyl iodide is cyclohexylmethyl iodide and the preferred cycloalkylalkyl bromide is cyclohexylmethyl bromide. Although any appropriate (aprotic) solvent may be used, we prefer using THF or methyl t-butyl ether.

The ketimine of formula (I) is a novel and useful intermediate in the formation of leukotriene biosynthesis inhibitors such as various substituted 2-benzoxazoles, 2-benzothiazoles, 2-oxazolopyridines and 2-thiazolopyridines. Using the ketimine of formula (I), a desired leukotriene biosynthesis inhibitor may be obtained by first hydrolyzing the ketimine to yield the chiral amine, $NHR_1R_2$, then coupling the chiral amine with an appropriately derivatized heterocycle using known methods (e.g., as described in U.S. Pat. No. 5,296,486, issued Mar. 22, 1994 and in Lazer et al, *J. Med. Chem,* 37, pp. 913–23 (1994).

Hydrolysis of of the novel ketimine intermediate (I) yields an enantiomerically pure α-cycloalkylalkyl substituted methanamine of formula (V) (shown below in Scheme 4):

Scheme 4

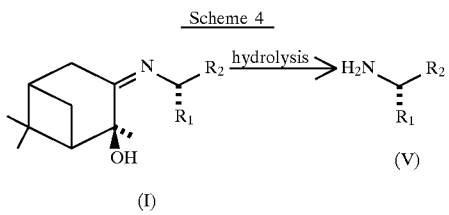

wherein $R_1$–$R_3$ and n are as defined above (including the preferred definitions of those radicals). The preferred α-cycloalkylalkyl substituted methanamine of formula (V) is α-cyclohexylmethyl-2-pyridinemethanamime.

The hydrolysis reaction of Scheme 4 may be accomplished using conventional methodology. However, we have found that acid-mediated hydrolysis is not particularly effective. Accordingly, we prefer base-mediated hydrolysis, and more particularly, base-mediated hydrolysis using hydroxylamine hydrochloride (preferably, about 1 to about 1.5 equivalents). This and other means of hydrolysis are well known to those of ordinary skill in the art.

Once obtained, amine of formula (V) may be further purified using known techniques. We especially prefer enrichment by diastereomeric salt formation. The salt is formed by reacting an appropriate amount of amine with an acid in an appropriate solvent. Examples of appropriate solvents include water, ethyl acetate, isopropanol and other alcohols. Examples of appropriate acids include tartaric acid and bromocamphorsulfonic acid. Preferably, the salt formed is a tartrate salt wherein approximately 0.5–1.5 equivalent of tartrate is present for every one equivalent of amine (and preferably, 0.5–1 equivalent of tartrate for every one equivalent of amine). We prefer formation of the hemitartrate (also known as the semitartrate) and the monotartrate salt of the amine (V).

In all of the above mentioned reaction steps, the progress of the reactions can be measured by well known methods, such as NMR, HPLC and thin layer chromatography. Following each reaction step, the intermediate products may be further purified (if desired) using known methods, such as crystallization from an appropriate solvent system or distillation.

The disclosure of all published documents cited hereinabove (including but not limited to patents and scientific publications) are hereby expressly incorporated by reference.

Although the following examples refer exclusively to the use of (S)-(−)-α-pinene to produce (S)-α-cyclohexylalkyl substituted methanamines, it will be appreciated by those of ordinary skill in the art that this invention can be readily extended to produce the opposite enantiomer of the end product (i.e., (R)-α-cyclohexylalkyl substituted methanamine) by starting with the other enantiomer of α-pinene (i.e., (R)-(+)-α-pinene).

The following examples are provided to illustrate the invention described herein. These examples demonstrate various process steps of the present invention and are not to be construed as limiting the scope of the invention in any way.

EXAMPLES

General Methods

GC (−)-α-pinene was analyzed using chiral gas chromatography to verify enantiomeric purity. The analysis was done using a Perkin-Elmer Sigma 2000 capillary GC with a flame ionization detector. A sample size of 0.5 µL was injected on a Supelco β-cyclodextrin 110 column (0.25×30 m) at 60° C. (isothermal) with a flow rate of 1 mL/min.

HPLC

Chiral HPLC analysis was done using a Rainin Dynamax system with a UV detector set at 254 nM. The Chiralpak AD column (Daicel Chemical Ind. Ltd, 0.46×25 cm), used for the amine analysis, was purchased from Chiral Technologies Inc. 730 Springdale Dr., P.O. Box 564, Exton Pa. (phone: 800-624-4725). The solvent system consisted of hexanes containing 5% anhydrous ethanol and 0.5% of diethylamine. This was used at a flow rate of 1.0 mL/min.

EXAMPLE 1

Oxidation of α-Pinene Using Phase Transfer Catalyst

A two phase solution of α-pinene in equal amounts of dichloromethane and water was treated with 5 weight % of methyl tributylammonium chloride. The cooled mixture was the treated with potassium permanganate in portions. The organic fraction was the collected and concentrated to give the desired product which was further purified by fractional distillation.

To a 50 gallon glass-lined reactor was charged 55 L of deionized water, 55 L of dichloromethane, 748 g of 70% methyl tributylammonium chloride (5 weight %), and 11.0 kg of S-(−)-α-pinene (80.77 mole). The mixture was cooled to ca. 0° C. (jacket temperature at ca. −5° C.). To this was added 24.2 kg of potassium permanganate (153.1 mole) via a stainless steel dispenser attached to the manhole. This was added in such a manner to maintain a reaction temperature of 2°–5° C. When addition was complete the jacket temperature was set to −2° C. and the reaction slurry was stirred for 15 h. A small sample of reaction mixture was worked up to check for completion since reaction mixture was still violet in color, suggesting excess $KMnO_4$ was still present. The material was examined by $^1$H-NMR. The crude material appeared to be quite clean, containing toluene which was used in the work-up. To the reactor was then added 55 L of toluene and the slurry was stirred for 30 minutes. The organic fraction was collected and the remaining solids in reactor were washed with 2×55 L of toluene. The organic fraction was then washed with 60 L of deionized water. The pH of the spent wash was checked with ColorpHast 0–14 test papers and the value was found to be pH <8. The combined organics were concentrated to a volume of ca. 50 L in the reactor. The reactor was drained and the organics were further concentrated on a rotary evaporator. This furnished 6.25 kg of a yellow oil.

The crude oil was didtilled through a 30 cm Vigreaux column using laboratory glass apparatus to furnish the desired ketoalcohol.

Yield: 5.7 kg, 42% (93.5% e.e. as determined by chiral GC analysis) basis: pinene.

EXAMPLE 2

Dihydroxylation/Oxidation of α-Pinene Using Potassium Osmate Dihydrate

A. General Description of Dihydroxylation Step: Preparation of (1R, 2R, 5R)-(+)-2-Hydroxy-3-pinandiol A mixture of (S)-(−)-α-pinene, pyridine, 4-methylmorpholine oxide, and potassium osmate dihydrate in acetone and water is stirred at reflux for about 40 hours. The reaction mixture is diluted with methyl t-butyl ether and hexanes and is washed with aqueous citric acid, aqueous sodium bicarbonate, and aqueous sodium chloride. The organic phase is dried over magnesium sulfate and concentrated under vacuum to provide (1R,2R,5R)-(+)-2-hydroxy-3-pinandiol in good yield and purity.

B. General Description of Oxidation Step: Preparation of (1R, 2R, 5R)-(+)-2-Hydroxy-3-pinanone A solution of (1R,2R,3R,5S)-pinanediol and triethylamine in methylsulfoxide and dichloromethane is treated with sulfur trioxide-pyridine while maintaining the reaction temperature at or below 25° C. The reaction mixture is diluted with ethyl acetate and washed with hydrochloric acid. The aqueous washes are saturated with sodium chloride and back extracted with ethyl acetate. The combined organic is diluted with hexanes and washed with hydrochloric acid and aqueous sodium chloride. After drying over magnesium sulfate, the organic phase is concentrated under vacuum. Distillation of the residue provides the title compound in good purity.

C. Dihydroxylation of α-pinene

To a 12 L flask equipped with an overhead mechanical stirrer, condenser, nitrogen inlet, and heating mantle was charged 500 g of S-(−)-α-pinene (3.67 moles), 2.70 g of potassium osmate (VI) dihydrate (0.2 mole %, 7.34 mmole), 857 g N-methylmorpholine-N-oxide (60 wt % in water, 1.2 eq.), 355 mL pyridine (1.2 eq.), 2.2 L of acetone, and 245 mL of deionised water. The turbid mixture was stirred at reflux for 44 h. A small sample was drawn from the mixture and checked by GC for the presence of α-pinene. The reaction mixture was diluted with 6.0 L of methyl t-butyl ether and 1.2 L of hexanes . The layers were separated and the organic fraction was washed with 4×2.0 L of 10% aqueous citric acid. The organic fraction was then washed with 2.0 L of sat. aq. $NaHCO_3$, followed by 1.0 L of sat. aq. NaCl, then dried over 100.0 g $MgSO_4$ The filtered organics were then concentrated to dryness on a rotary evaporator to give a dark green oil.

Yield: 562.0 g, 90% yield; basis: α-pinene $^1$H-NMR was consistent with literature examples of the desired diol.

D. Oxidation of Pinanediol with Sulfur Trioxide-Pyridine

To a 12 L flask equipped with a mechanical stirrer, nitrogen inlet, thermocouple and ice bath for cooling was added 562.0 g of diol (Example 2C ;3.30 moles) dissolved in 1770 mL of DMSO (7.6 eq.) and 1770 mL of dichloromethane and the reaction was cooled to 14° C. To this was added 1833 mL of triethylamine (4 eq) followed portion wise by 1570 g of sulfur trioxide-pyridine complex (3 eq) keeping the temperature below 20° C. (total addition time 70 minutes). The mixture was stirred in the ice bath for 1 h and TLC(5% $CH_3OH$ in $CH_2Cl_2$, silica, PMA vis.) indicated no starting material present. The reaction mixture was diluted with 5.6 L mL ethyl acetate and washed with 2×2.8 L of 0.5N HCl. The aqueous layer was saturated with 2.5 kg of NaCl and extracted with 2×2.4 L of ethyl acetate. The combined organics were treated with 3.0 L of hexanes and washed with 2×5.6 L of 0.5N HCl and 2×100 mL of saturated NaCl solution. The organics were dried over ca. 15g of $MgSO_4$, filtered and concentrated to a brown oil.

Crude Yield: 564.04 g, 100% yield; basis: diol

Material was distilled through a 30 cm Vigreaux column @ 3–4 mm Hg. Collected two major fractions distilling at 100°–104° C.

Net Yield: 471.41 g, 85% yield; basis: diol (76%; basis: α-pinene)

$^1$H-NMR of both fractions were very clean and consistent with that for the desired product.

$^1$H-NMR (CDCl$_3$, 270 MHz): δ 2.60–2.58 (m, 2H); 2.48–2.41 (m, 2H, 1H is exchangeable); 2.12–2.09 (m, 2H); 1.66 (d, 1 H, J=10.8 Hz); 1.36 (s, 3H); 1.34 (s, 3H); 0.86 (s, 3H).

$^{13}$C-NMR (CDCl$_3$, 67.5 MHz): δ 213.96; 49.48; 42.76; 39.00; 38.05; 28.17; 27.07; 24.95; 22.63.

EXAMPLE 3

Condensation of Hydroxypinanone with Primary Amine

A. General Description: Preparation of (1R,2R,5R)-(+)-2-Hydroxy-3-(2-pyridylmethyl) ketimine A mixture of (1R,2R,5R)-(+)-2-hydroxy-3-pinanone, 2-(aminomethyl)pyridine, and a catalytic amount of titanium isopropoxide or thionyl chloride in toluene is heated at reflux with azeotropic removal of water. The cooled reaction mixture is filtered through silica gel and concentrated under vacuum to provide the title compound in adequate purity for further elaboration.

B. Condensation of 2-(Aminomethyl)pyridine with (R)-Hydroxypinanone using Titanium Isopropoxide To a 5-liter flask fitted with an overhead mechanical stirrer, N$_2$, Dean-Stark trap, and a heating mantle was charged 241.04 g of 2-(aminomethyl)pyridine (2.23 moles), 375.0 g of pinanone (Example 2D; 2.23 moles), 52.4 mL of Ti(O-i-Pr)$_4$ (10 mole %) and 1.6 L of toluene . The resulting mixture was heated to reflux for 3 h at which time the reaction was shown complete by TLC (10% CH$_3$OH in CH$_2$Cl$_2$, Dragendorff, silica). The mixture was cooled to 30° C. and filtered through 375 g of silica gel. The filter cake was washed with 2.2 L of toluene. The combined filtrate and wash were evaporated to dryness on a rotary evaporator. To the residue was added 500 mL of THF and evaporated as above . This procedure was again repeated to give the desired imine as an orange oil.

Yield: 555.39 g, 96.4% yield; basis: pinanone

C. Condensation of 2-(Aminomethyl)pyridine with (R)-Hydroxypinanone using Thionyl Chloride To a 5-liter flask fitted with an overhead mechanical stirrer, N$_2$, Dean-Stark trap, addition funnel, and a heating mantle was charged 241.0 g of 2-(aminomethyl)pyridine (2.23 moles), 375.0 g of pinanone (as from Example 2D; 2.23 moles) and 1.6 L of toluene. To this was slowly added a solution of SOCl$_2$ (8.1 mL, 0.11 moles) in 50 mL of toluene. The resulting mixture was heated to reflux for 5 h at which time the reaction was shown complete by TLC (10% CH$_3$OH in CH$_2$Cl$_2$, Dragendorff, silica). The resulting brown solution was then evaporated to dryness on a rotary evaporator. To the residue was added 500 mL of THF and evaporated as above . This procedure was again repeated to give the desired imine as an orange oil.

Yield: 555.3 g, 96% yield; basis: pinanone $^1$H NMR (CDCl$_3$, 270 MHz): δ 8.51–8.48 (m, 1H); 7.63 (dt, 1H, J=1.8, 7.7 Hz); 7.49 (d, 1H, J=8.1 Hz); 7.14–7.09 (m, 1H); 4.60 (apparent t, 2H); 2.86 (broad s, 1H, exchangeable); 2.57 (broad s, 2H); 2.33–2.29 (m, 1H); 2.08–2.00 (m, 2H); 1.55 (d, 1H, J=10.8 Hz); 1.53 (s, 3H); 1.29 (s, 3 H); 0.82 (s, 3H).

$^{13}$C NMR (CDCl$_3$, 67.5 MHz): δ 177.62; 160.15; 148.96; 136.59; 121.71; 56.26; 50.22; 38.52; 38.30; 33.94; 28.39; 28.17; 22.81.

EXAMPLE 4

Alkylation and Hydrolysis of Ketimine

A. General Description: Preparation of α-Cyclohexylmethyl-2-pyridinemethanamine

To a solution of (1R,2R,5R)-(+)-2-hydroxy-3-(2-pyridylmethyl)ketimine in tetrahydrofuran is added n-butyllithium (2 equivalents) in hexanes while maintaining the reaction temperature at −10° to 5° C. The deep red dianion solution is treated with either cyclohexylmethyl bromide or iodide. The resultant mixture is stirred at −10° to 5° C. for approximately 16 hours, after which it is quenched with aqueous ammonium chloride. The organic phase is combined with ethanol and aqueous hydroxylamine hydrochloride and stirred at ambient temperature for approximately 20 hours. Hydrochloric acid is added and the resulting mixture is washed with ethyl acetate. The aqueous phase is made basic with ammonium hydroxide and is extracted with dichloromethane. The organic layer is dried over magnesium sulfate and concentrated to provide the title compound.

B. Alkylation and Hydrolysis of Chiral Ketimine

To a jacketed 12 L flask fitted with an overhead mechanical stirrer, N$_2$, an addition funnel, a thermocouple and a recirculating chiller piped into the jacket was charged 538.90 g of imine (Example 3B; 2.08 moles), and 5.5 L of THF. Cooled solution to ca. −0° C. and added over 2.5 h 1.67 L of 2.5M n-BuLi (2 eq.) keeping reaction temp. at or below −5° C. The resulting solution was stirred at −10° to 5° C. for 1 h, then added 536.1 g of cyclohexylmethyl iodide (1.15 eq.) over 1 h maintaining reaction temperature at or below −5° C. Stirred at −10° to 5° C. for 16 h, then checked by TLC for complete consumption of imine (silica, 10% CH$_3$OH in CHCl$_3$, PMA vis.). Reaction was judged complete, so added over 30 min, 1.5 L of sat. aq. NH$_4$Cl solution, keeping reaction temp. at or below −3° C. After addition was complete, warmed reaction mixture to 5° C. and filtered. Separated layers of filtrate and charged organic back into the reaction vessel. To this was added 386 mL of ethanol, 193 mL of deionised water, and 173.90 g of hydroxylamine hydrochloride and stirred at room temperature for 20 h. To this was then added 5.5 L of 1N HCl and washed with 3×2.0 L of ethyl acetate. Added to washed aqueous 600 mL of conc. NH$_4$OH. Reaction was at pH=11. Extracted with 3×2.0 L of CH$_2$Cl$_2$. Dried extracts over 130 g of MgSO$_4$ and concentrated to dryness on a rotary evaporator to give the desired product as a brown oil.

Yield: 358.26 g, 84% yield; basis: imine. Chiral HPLC shows material to be 90% e.e.

$^1$H NMR (CDCl$_3$, 270 MHz): δ 8.49–8.47 (m, 1 H); 7.59 (dt, 1H, J=1.8, 9.1 Hz); 7.32 (d, 1H, J=8.1 Hz); 7.12–7.07 (m, 1H); 4.78 (dd, 1H, J=2.1, 8.1 Hz); 2.71–0.86 (complex series of m, 20H; including singlets at 1.52 (3H); 1.28 (3H); 0.88 (3H)).

$^{13}$C NMR (CDCl$_3$, 67.5 MHz): δ 179.29; 175.59; 163.44; 148.72; 136.62; 121.75; 121.19; 62.47; 53.38; 49.93; 45.44;

38.24; 34.60; 34.10; 33.49; 32.70; 28.51; 27.93; 27.27; 26.48; 26.38; 26.23; 25.24; 22.78; 20.82.

EXAMPLE 5

Enantiomeric Enrichment of α-Alkylated Amine

A. General Description: Enantiomeric Enrichment of (S)-α-Cyclohexylmethyl-2-pyridinemethanamine Using Tartaric Acid A solution of the above amine in isopropanol is treated with a solution of L-tartaric acid in isopropanol and water. The resultant crystalline solid is collected by filtration and washed with a mixture of hexanes and isopropanol and dried under vacuum. This affords the title compound as a hemi-tartrate in suitable optical purity for further elaboration.

B. General Description: Enantiomeric Enrichment of (S)-(α-Cyclohexylmethyl-2-pyridinemethanamine Using Bromocamphorsulfonic Acid A solution of the crude amine in ethyl acetate is treated with an ethyl acetate solution of 3-bromo-8-camphorsulfonic acid. The resulting solid is collected by filtration and washed with ethyl acetate. The crude salt is recrystallized from isopropanol, washed with ethyl acetate and dried to afford the title compound as a 3-bromo-8-camphorsulfonate salt in suitable optical purity.

C. Enantiomeric Enrichment of (S)-α-Cyclohexylmethyl-2-pyridinemethanamine Using L-Tartaric Acid To a 1 L round bottom flask equipped with an overhead mechanical stirrer and an addition funnel was charged 65.33 g of amine (Example 4B; 0.32 moles; corrected for residual THF content by NMR) and 254 mL of isopropanol. In a separate flask was charged 24.01 g of L-tartaric acid (0.5 eq.) and 21.78 g of deionised water. When the solids were completely dissolved, 241 mL of isopropanol was added and the mixture was transferred to the addition funnel. The tartaric acid solution was added dropwise over 20 min. After completion of addition, the resulting thick slurry was stirred at ambient temperature for 18 h. The solids were collected by filtration and washed with 3×100 mL of 25% isopropanol/hexanes. The solid was dried under house vacuum at ambient temperature for 18 hours to furnish the desired salt as a white solid.

Yield: 69.84 g , 78% yield; basis: pyridylamine ; 98.8% e.e. as determined by chiral HPLC.

D. Liberation of Amineftom the L-Tartrate Salt 68.67 g of the tartrate salt (Example 5C; 0.246 moles) was placed in a flask and dissolved in 100 mL of 15% NaOH solution and 100 mL of toluene was added. The layers were separated and the aqueous layer was extracted once more with 100 mL of toluene. The combined toluene extracts were washed with 2×100 mL deionised water and 100 mL of saturated NaCl solution, the organic fraction was dried over 10 g of MgSO$_4$ and concentrated to dryness on a rotary evaporator to give a clear yellow oil.

Yield: 45.46 g, 90.3% yield; basis: salt

E. Enantiomeric Enrichment of (S)-α-Cyclohexylmethyl-2-pyridinemethanamine using 3-Bromo-8-camphorsulfonic Acid To a 5 L round bottom flask equipped with a mechanical stirrer and nitrogen inlet was charged 409.24 g of amine (Example 4B; 2.01 moles) dissolved in 500 mL of ethyl acetate. To this was added 1.60 L of a 1.25M solution of (+)-3-bromo-8-camphorsulfonic acid in ethyl acetate. The solution became warm and a precipitate began forming. The suspension was stirred overnight at room temperature. The precipitate was filtered and washed with 1.5 L of ethyl acetate to give a white solid which was dried for 20 hours under house vacuum at room temperature.

Crude Yield: 674.83 g of salt was obtained at 89.8% e.e. as determined by chiral HPLC.

The salt was recrystallized by dissolving the solid in 7.50 L of isopropanol and heating to 83° C. The heating mantle was removed and the solution allowed to cool to ambient temperature by standing overnight. The crystals were collected by filtration and washed with 1.25 L of ethyl acetate . The solid was dried for 72 hours under house vacuum at room temperature to furnish the salt as a white solid.

Net Yield: 522.91 g, 77.5% yield; Basis: pyridylamine; 98.8% e.e. as determined by chiral HPLC.

F. Liberation of Amine from (+)-Bromocamphorsulfonate Salt 52.57 g of the BCSA salt (Example 5E) was placed in a flask and dissolved in 100 mL of 15% NaOH solution and 250 mL of toluene was added. The layers were separated and the aqueous layer was extracted once more with 250 mL of toluene. A thick slurry of crystals precipitated out in the separatory funnel and had to be filtered and washed with toluene. The combined toluene extracts were washed with 2×100 mL of deionised water and 2×100 mL of saturated NaCl solution, the organic fraction was dried over 10 g of MgSO$_4$, filtered, and concentrated to dryness on a rotary evaporator.

Yield: 22.80g, 100% yield; basis: salt

While we have hereinbefore presented a number of embodiments of this invention, it is apparent that our basic construction can be altered to provide other embodiments that utilize the processes and compositions described herein. For example, obvious variations of the synthetic process steps and intermediates described and exemplified herein will be easily recognized by those of ordinary skill in the art. This application expressly envisions and extends to those obvious variations. It should also be appreciated that the scope of this invention is defined by the following claims rather than by the specific embodiments that have been presented hereinabove by way of example.

We claim:

1. A process for producing 2-hydroxy-3-pinanone, comprising the steps of reacting α-pinene with catalytic potassium osmate in solution of pyridine, N-methylmorpholine-N-oxide and aqueous acetone to produce cis-pinanediol; and thereafter oxidizing said cis-pinanediol with DMSO activated by pyridine.SO$_3$ and triethylamine in an appropriate solvent to produce 2-hydroxy-3-pinanone.

2. The process of claim 1, wherein the solvent is methylene chloride.

3. A process for producing 2-hydroxy-3-pinanone comprising of the step of oxidizing α-pinene with potassium permanganate using a phase transfer catalyst in methylene chloride/water solvent.

4. The process according to claim 3, wherein the phase transfer catalyst is an ammonium salt.

5. The process according to claim 4, wherein the ammonium salt is methyl tributylammonium chloride.

6. The process according to claim 3, wherein the solvent is 1:1 methylene chloride/water.

7. A process for alkylating a ketimine of 2-hydroxy-3-pinanone comprising the steps of:
(a) deprotonating a ketimine of 2-hydroxy-3-pinanone using a strong base; and
(b) reacting about 1 equivalent of the deprotonated ketimine with about 1–2 equivalents of an appropriate alkyl halide at a temperature of between about −20° C. and about 5° C.

8. The process according to claim 7, wherein the strong base is n-butyl lithium.

9. The process according to claim 7, wherein the deprotected ketimine is reacted with 1 equivalent of a cycloalkylalkyl iodide or 2 equivalents of cycloalkylalkyl bromide.

10. A process for producing an (S)-α-cycloalkylalkyl-2-pyridinemethanamine comprising the step of hydrolyzing the corresponding (S)-(α-cycloalkylalkyl-2-hydroxy-3-(pyridinemethyl) ketimine with hydroxylethylethylamine chloride.

11. The process according to claim 9 or 10, wherein said cycloalkylalkyl is cyclohexylmethyl.

12. A process for producing (S)-α-cyclohexylmethyl-2-pyridinemethanamine from (S)-(−)-α-pinene comprising the steps of:
(a) oxidizing (S)-α-pinene with potassium permanganate using a phase transfer catalyst in an appropriate solvent to form (1R, 2R, 5R)-(+)-2-hydroxy-3-pinanone;
(b) reacting (1R, 2R, 5R)-(+)-2-hydroxy-3-pinanone with 2-(aminomethyl) pyridine and a Lewis acid catalyst in toluene or methyl t-butyl ether to form (1R, 2R, 5R)-(+)-2-hydroxy-3-(pyridinemethyl) ketimine;
(c) deprotonating (1R, 2R, 5R)-(+)-2-hydroxy-3-(pyridinemethyl) ketimine using a strong base;
(d) reacting about 1 equivalent of the deprotonated ketimine with about 1–2 equivalents of cyclohexylmethyl halide at a temperature of between about −20° C. and about 5° C. to form (S)-α-cyclohexylmethyl-2-hydroxy-3-(pyridinemethyl) ketimine; and
(e) hydrolyzing (S)-α-cyclohexylmethyl-2-hydroxy-3-(pyridinemethyl) ketimine.

13. The process according to claim 12, wherein the phase transfer catalyst of step (a) is methyl tributyl ammonium chloride; the Lewis acid catalyst in step (b) is titanium isopropoxide or thionyl chloride and the strong base in step (c) is n-butyl lithium.

14. The process according to claim 12 or 13, further comprising the step of purifying (S)-(α-cyclohexylmethyl-2-pyridinemethanamine by reacting (S)-α-cyclohexylmethyl-2-pyridinemethanamine with L-tartaric acid in an appropriate solvent to form a tartrate salt.

15. The process according to claim 14, wherein 0.5–1.5 equivalent of tartaric acid is used.

16. The process according to claim 15, wherein 0.5–1 equivalent of tartaric acid is used.

17. A compound having the structure of formula (I):

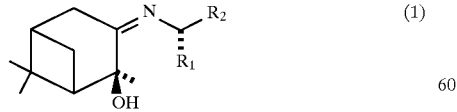

(1)

wherein:

R₁ is –(CH₂)ₙ-cycloalkyl, said cycloalkyl being unsubstituted or substituted with C₁–C₄ alkyl, C₁–C₄ alkoxy, hydroxy, amino or halo;

R₂ is selected from the group consisting of an unsubstituted or substituted naphthyl ring wherein the ring substituents are selected from the group consisting of halo, hydroxy, amino, C₁–C₄ alkyl and C₁–C₄ alkoxy; 3-methyl- 1,2,4-oxadiazol-5-yl; 2- or 3-thienyl; 2-, 3-, or 4-pyridyl, unsubstituted or substituted with halo, hydroxy, amino, C₁–C₄ alkyl and C₁–C₄ alkoxy; 2-imidazole, unsubstituted or substituted on the nitrogen with methyl; 2-thiazole, unsubstituted or substituted at the 4-position with methyl; —C(O)R₃; —CH₂O (C₁–C₄ alkyl); CH₂S(C₁–C₃ alkyl); —CH₂SO₂(C₁–C₃ alkyl); —CH₂NH₂; —CH₂NHSO₂ (C₁–C₃ alkyl)2; and —CH₂OC(O)NH(C₁–C₃ alkyl);

R₃ is selected from the group consisting of C₁–C₃ alkyl, phenyl and 1-methylimidazol-2-yl; and n is an integer from 0–4.

18. The compound according to claim 17, wherein R₂ is selected from the group consisting of 2-, 3-, or 4-pyridyl.

19. The compound according to claim 18, having the structure of formula (II):

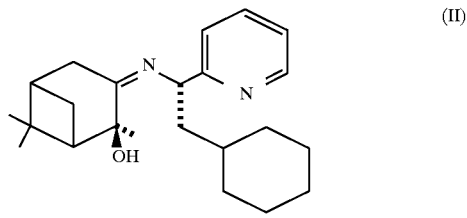

(II)

20. The compound according to claim 18, having the structure of formula (III):

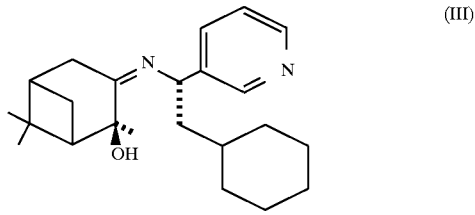

(III)

21. The compound according to claim 18, having the structure of formula (IV):

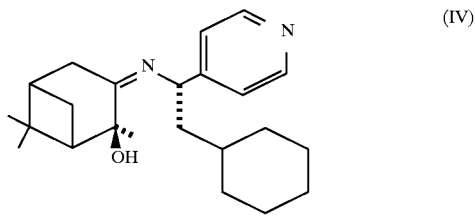

(IV)

* * * * *